United States Patent [19]

Takezawa et al.

[11] 4,169,764

[45] Oct. 2, 1979

[54] PROCESS FOR PRODUCTION OF UROKINASE

[75] Inventors: Kenji Takezawa, Yokohama; Masaharu Nakanishi, Koza; Yasumi Yugari, Kamakura, all of Japan

[73] Assignee: Ajinomoto Co., Inc., Tokyo, Japan

[21] Appl. No.: 851,480

[22] Filed: Nov. 14, 1977

Related U.S. Application Data

[63] Continuation-in-part of Ser. No. 711,396, Aug. 3, 1976, abandoned.

[30] Foreign Application Priority Data

Aug. 13, 1975 [JP] Japan .................................. 50-98408

[51] Int. Cl.² ............................................. C07G 7/026
[52] U.S. Cl. ..................................... 435/215; 435/815
[58] Field of Search ........................................ 195/66 B

[56] References Cited

U.S. PATENT DOCUMENTS

| 3,723,251 | 3/1973 | Ogawa et al. ...................... 195/66 B |
| 3,950,223 | 4/1976 | Yugari et al. .......................... 195/68 |

*Primary Examiner*—Lionel M. Shapiro
*Attorney, Agent, or Firm*—Cooper, Dunham, Clark, Griffin & Moran

[57] ABSTRACT

Method for the isolation of urokinase from human urine in which the urokinase is adsorbed and thereafter eluted with aqueous cation surfactant mixture. Novel carboxyalkyl cellulose is utilized as a preferred adsorbent.

12 Claims, 1 Drawing Figure

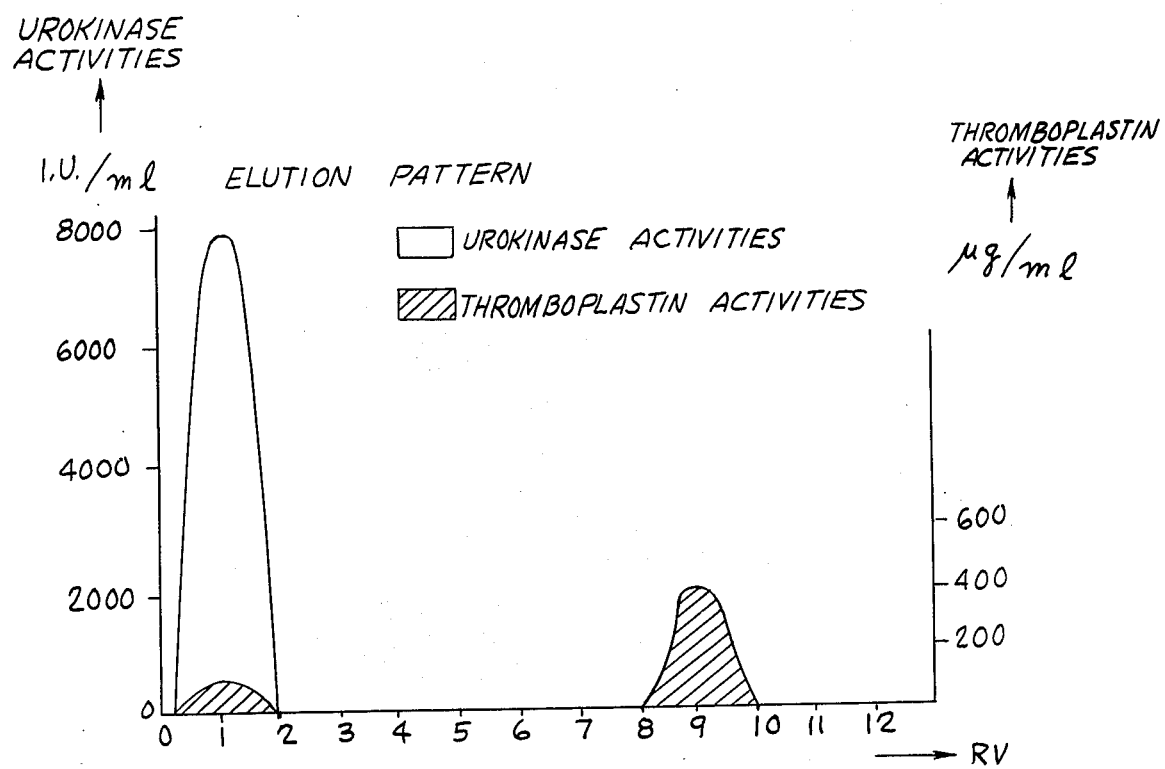

PROCESS FOR PRODUCTION OF UROKINASE

RELATED APPLICATION

This application is a continuation-in-part of copending application Ser. No. 711,396 filed Aug. 3, 1976, now abandoned.

This invention relates to the process for producing urokinase from human urine, and to the purification of the crude urokinase thus obtained.

Urokinase is an enzyme which is found in human urine. It is known to stimulate the production of the fibrinolytic protease plasmin which is important for dissolving thrombi. Urokinase therefore is of known and significant importance in the thrombolytic therapy.

The amount of urokinase present in human urine is extremely small, and its isolation therefore is particularly tedious and expensive.

At present, urokinase is produced industrially by contacting healthy human urine with any of a variety of known adsorbents, and eluting the urokinase adsorbed with alkaline solutions. In these known methods, impurities including proteins other than urokinase, together with urokinase, are both adsorbed and eluted. These include thromboplastin-like materials which are undesirable in urokinase preparations. Moreover, since urokinase is very unstable in alkaline solution, the yield is less than 70%.

A process has been discovered in accordance with this invention which makes possible the recovery of urokinase activity in high yield and purity as well as the separate recovery of thromboplastin activity. In accordance with this invention, the recovery of urokinase is improved by elution with cationic surfactant solutions containing selected concentrations of surfactants.

Since the content of thromboplastin-like materials in the urokinase purified according to the present invention is remarkably small, the recovered urokinase can rapidly dissolve blood clots formed without causing blood coagulation. Accordingly, the process of this invention can be employed to obtain highly purified, stabilized, and highly active urokinase products which can be employed with minimum side effects.

Adsorbents normally employed in the conventional process of recovering urokinase can also be used in the present invention. Examples of the adsorbents are cation exchanging resins such as carboxyalkyl cellulose including known materials in powder or particle form, carboxyalkyl Sephadex, polyacrylonitrile resin fiber, silica gel-bentonite, dialkylaminoalkyl cellulose, dialkylaminoalkyl Sephadex and phosphocellulose. In these adsorbents, the alkyl groups will normally contain one or two carbon atoms, but may contain four or more such atoms.

A novel carboxyalkyl cellulose in fiber form has been prepared for use in this invention, and has proved to be an excellent adsorbent for urokinase. The product is prepared from any natural or regenerated cellulose fiber such as ply thread, knits or raw cotton cloth. Absorbent cotton and gauze are the preferred starting materials since they are readily obtainable at reasonable cost.

The products are prepared by reaction of the cellulose fibers with an α-halogen alkanoic acid containing up to four carbon atoms in the presence of an alkaline reagent such as an alkali metal hydroxide. Suitable acids include α-chloroacetic, α-bromoacetic, and α-chlorobutyric acid. Derivatives of these acids, such as esters, acid halides, and alkali metal salts, can also be employed.

In the presently preferred method for producing the product, the selected cellulose material is taken up in aqueous alkali, for example, sodium or potassium hydroxide solution containing from 5.5 to 16 moles of alkali per anhydrous glucose unit. A total of from 0.1 to 1 mole of α-halo acid per mole of alkali is added, and the mixture maintained at 30° C. to 90° C. for 1 to 10 hours. This procedure provides a product with a degree of substitution of from 0.07 to 0.2 which is desirable for the process of this invention.

Of course, it is possible by varying the amounts of reactants to vary the degree of substitution within wide limits. It has been observed, however, that if the degree of substitution of carboxyalkyl groups is appreciably more than 0.2, it becomes difficult to pass the urine through the column. If the degree of substitution is appreciably less than 0.07, the amount of urokinase adsorbed is too low to be practical.

For the best balance of cost and recovery, it is preferred that the degree of substitution be from 0.1 to 0.18. The preferred carboxyalkyl cellulose fiber is the carboxymethyl product because it is normally the least expensive to prepare.

To carry out the invention, the human urine, or diluted human urine in which the ratio of water to urine is from 0.5 to 12 g of water per g of urine, is contacted with the selected adsorbent at the selected concentration either in a column or by the batch method.

A typically useful column would be 4.1 cm by 10 cm and contain 3.5 g (40 ml) of carboxymethylated absorbent cotton with a degree of substitution of 0.168. The adsorbent is first washed with 0.1 N hydrochloric acid, then with water and finally wetted with 0.1 M sodium chloride solution.

The urine is normally fresh and from healthy adult humans with a density of 1.016 at 33° C. It may be adjusted to pH 5.60 with concentrated hydrochloric acid, and diluted with the selected volume of water.

The ratio of urokinase adsorbed to urokinase charged is calculated according to the following formula:

$$100 - [(\frac{\text{Total activity of urokinase which was not adsorbed}}{\text{Total activity of urokinase charged}}) \times 100]$$

Activities of urokinase are calculated using WHO International Urokinase Standard based on the standardized method proposed by the Committee of Thrombolytic Agents, N.I.H., USA using both human plasminogen and fibrinogen which is the physiological substrate in nature. The results are expressed in international units (I.U.). The urokinase is dialyzed before measurement for the calculation of activity.

In typical procedures of the process carried out as described above, the adsorbed urokinase is eluted by soaking the adsorbent urokinase product in buffer solution at pH 8.0, containing 0.03% benzalkonium chloride and 0.5 M sodium chloride. Thus eluted urokinase solution is adjusted to pH 7.0 with hydrochloric acid solution, and the activities of thus obtained urokinase calculated. Total activities of urokinase recovered from human urine charged were calculated.

The results are listed in Table 1.

TABLE 1

| Sample No. | Weight of Water Added per 1 g of Fresh Human Urine | Degree of Dilution | Volume of Feed Solution | Speed of Feed | Rate of Adsorbing | Recovery of Urokinase Activity* |
|---|---|---|---|---|---|---|
| | g | | RV | SV | % | % |
| 1 | 0 | 1 | 72 | 18 | 9 | 4 |
| 2 | 0.5 | 1.5 | 108 | 27 | 25 | 16 |
| 3 | 1 | 2 | 144 | 36 | 72 | 92 |
| 4 | 2 | 3 | 216 | 54 | 82 | 100 |
| 5 | 3 | 4 | 288 | 72 | 78 | 94 |
| 6 | 5 | 6 | 432 | 108 | 63 | 80 |
| 7 | 7 | 8 | 576 | 144 | 54 | 71 |
| 8 | 10 | 11 | 792 | 198 | — | 60 |
| 9 | 12 | 13 | 936 | 234 | — | 52 |
| 10 | 15 | 16 | 1,152 | 288 | — | 34 |

*Recovery of Urokinase Activity = $\frac{\text{Total Activity Eluted}}{\text{Total Activity Charged}} \times 100$ As is evident from the Table, human urine obtained by diluting the originally obtained human urine with water in a ratio of 0.5 to 12 g of water per 1 g of human urine (human urine of degree of dilution: 1.5 to 13) is preferred for the practice of the invention.

Carboxyalkylated cellulose fibers are very useful for the present invention because of the good results obtained. In the product obtained in the following Experiment 1, 100 grams of carboxymethylated cotton have a stable volume of about 1000 ml. The volume can be changed freely by pressure. The 100 grams can pass more than 300 l of human urine at a rate in excess of 36 l/1 hour with substantially no decrease in rate. The product can be employed to treat large quantities of human urine over a very short period of time.

EXPERIMENT 1

In a bleaker 50 grams of commercial cotton gauze (0.309 mole of anhydrous glucose unit), 46 to 184 grams of sodium hydroxide and 0.5 to 1.1 l of water were mixed and stirred. The mixtures were allowed to stand for 2 hours at room temperature. To each mixture, 60 to 181 grams of monochloroacetic acid crystals were added and the resulting mixtures left standing for 4 hours at 70° C. with occasional stirring. The products were separated and washed with water. A part of each product was washed with 2 l of methanol and 1 l of acetone and then dried under vacuum with dryer. The other part was used as an adsorbent for this invention without such washing.

Products with differing degrees of carboxymethyl substitution were obtained as shown in Table 2.

TABLE 2

| Amount of NaOH | Amount of Monochloroacetic Acid | Mole Ratio of NaOH to Acetic Acid | Volume of Water | Percent of NaOH (W/W) | Degree of Substitution | Product No. |
|---|---|---|---|---|---|---|
| g | g | | ml | % | | |
| 46 | 60 | 1.81 | 610 | 7 | 0.03 | 3 |
| 46 | 120 | 1.27 | 1,080 | 4 | 0.02 | 4 |
| 68 | 90 | 1.78 | 570 | 11 | 0.06 | 7 |
| 91 | 120 | 1.79 | 570 | 14 | 0.12 | 9 |
| 91 | 91 | 2.36 | 500 | 15 | 0.16 | 11 |
| 121 | 91 | 6.33 | 800 | 13 | 0.07 | 14 |
| 184 | 181 | 2.40 | 800 | 19 | 0.23 | 20 |

The degree of substitution was determined by converting total exchange capacities (equivalents per 1 gram) into chemical equivalent values per anhydrous glucose unit which is in the cellulose. Measurements were made according to "The Process for Measuring Total Exchanging Capacities in Weakly Acidic Cation Exchange Resins" in Ion Exchange Manual [1], published by Mitsubishi Kasei Kogyo K.K.

EXPERIMENT 2

A total of 50 grams of commercial absorbent cotton (0.309 mole of anhydrous glucose unit), sodium hydroxide and 800 ml of water were mixed and thoroughly stirred in a 1 l beaker. This mixture was allowed to stand for 2 hours at room temperature. To this mixture, monochloroacetic acid crystals were added. The procedures were the same as in Experiment 1. Dried products were obtained.

The results are listed in Table 3.

TABLE 3

| Amount of NaOH | Amount of Monochloroacetic acid | Mole Ratio of NaOH per Acetic acid | Percent of NaOH (W/W) | Degree of substitution | Product No. |
|---|---|---|---|---|---|
| g | g | | % | | |
| 68 | 90 | 1.78 | 11 | 0.06 | 21 |
| 91 | 90 | 2.38 | 10 | 0.08 | 22 |
| 120 | 118 | 2.38 | 13 | 0.089 | 26 |
| 128 | 126 | 2.38 | 14 | 0.110 | 27 |
| 136 | 134 | 2.38 | 14.5 | 0.124 | 28 |
| 146 | 144 | 2.38 | 15.4 | 0.168 | 24 |
| 160 | 158 | 2.38 | 16.7 | 0.193 | 31 |
| 184 | 181 | 2.38 | 18.7 | 0.218 | 39 |
| 204 | 202 | 2.38 | 20.3 | 0.230 | 40 |
| 128 | 142 | 2.10 | 13.8 | 0.120 | 34 |
| 144 | 126 | 2.70 | 15.2 | 0.116 | 32 |

Any of a wide variety of cationic surfactant solutions can be used as eluents. The presently preferred surfactants are tetra substituted ammonium salts. These may be tetraalkyl ammonium salts in which, normally, one alkyl group is a higher alkyl group and the others are lower alkyl groups. They may be higher alkyl-aralkyl quaternary ammonium salts; higher alkyl-aralkyl-lower alkyl salts; higher alkyl-lower alkyl-aryl salts; aryl-lower alkyl-aralkyl salts; higher alkyl pyridinium salts; or polyalkyl-naphthalenemethyl pyridinium salts. A lower alkyl group contains up to 6 carbon atoms. A higher alkyl group contains from 11 to 20 carbon atoms. Aryl is normally, but not necessarily phenyl. Aralkyl is normally benzyl, but may be another group. Halides, especially chlorides, are preferred.

Specific examples of cationionic surfactants include cetyl-trimethyl-ammonium salts, stearyl-trimethyl-ammonium salts, dimethyl-benzyl-lauryl-ammonium salts, dimethyl-phenyl-benzyl-ammonium salts, lauryl-pyridinium salts, lauryl-trimethyl-ammonium salts, lauryl-dimethyl-benzyl-ammonium salts, cetyl-trimethyl-ammonium salts, stearyl-trimethyl ammonium salts, tetradecyl-dimethyl-benzyl-ammonium salts (benzalkonium salts), and products obtained by condensing N,M-diethyl ethylene diamine with fatty acid such as oleic acid quaternizing the condensation product with alkylating agent such as benzyl chloride, dimethyl sulfuric acid, etc., (Sapamin BCH, Sapamin MS). Also, salts such as cetyl pyridinium salts, stearamide-methyl-pyridinium salts, lauryl pyridinium salts, cetyl quinolynium salts, lauryl aminopropionic acid methyl ester salts, lauryl amino propionic acid metal salts, lauryl dimethyl betaine stearyl dimethyl betaine, lauryl dihydroxyethyl betaine and benzethonium salts.

Quaternary ammonium salts which are commercially available and particularly useful in the invention include:

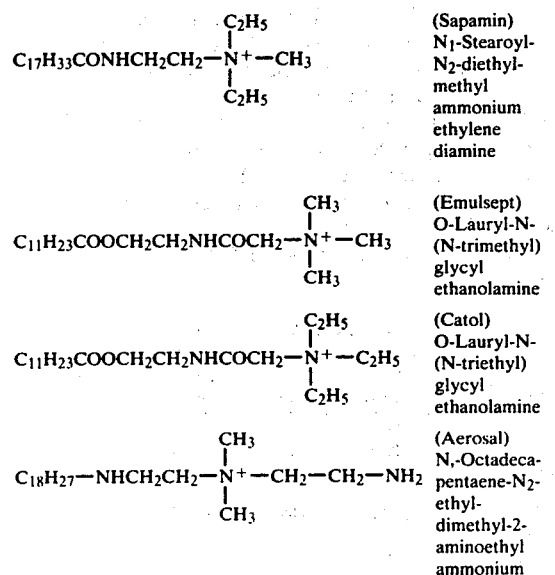

The elution step in the present invention normally takes place at pH 6 to 9, preferably 7 to 8. Increasing the pH of the eluting agent normally decreases the yield and purity of urokinase eluted.

In the practice of this invention, the concentration of surfactants in the aqueous elution solution can vary over a wide range. In some instances, their range can be as wide as from 0.000001 to 0.5 percent (W/V). If the concentration of the surfactant is too high, it may cause denaturation of the urokinase so that little or no urokinase is eluted. If the concentration is too low, all of the urokinase activity may remain on the adsorbent.

What has been discovered is that with each class of cationic surfactant, there is an optimum concentration for the elution of urokinase activity.

The preferred cationic surfactants, and their preferred concentration ranges in percent by weight are as follows:

| | |
|---|---|
| Benzalkonium salts | $3 \times 10^{-3}$ to $3 \times 10^{-2}\%$ |
| Benzethonium salts | $1 \times 10^{-5}$ to $1 \times 10^{-2}\%$ |
| Lauryl pyridinium salts | $1 \times 10^{-3}$ to $3 \times 10^{-1}\%$ |
| Trimethyl stearyl ammonium salts | $5 \times 10^{-4}$ to $5 \times 10^{-2}\%$ |

The reason for the preference will be readily apparent from the following non-limiting examples:

EXAMPLE 1

Fresh human urine was charged on carboxymethyl cellulose powder column whch had been equilibrated with 0.1 M sodium phosphate, −0.1 M sodium chloride buffer (pH 7.2) (buffer I), to adsorb urokinase on the carboxymethyl cellulose. The column was washed with buffer I and eluted at 25° C. with buffer I further containing benzalkonium chloride, benzethonium chloride, lauryl pyridinium chloride or trimethyl stearyl ammonium chloride solution at several different concentrations.

The results are listed in Table 4.

TABLE 4

| Concentration (%) | Recovery of Activities (%) | Activities per mg of protein (I.U.) |
|---|---|---|
| Benzalkonium chloride solution | | |
| 0.001 | 0 | |
| 0.003 | 30 | |
| 0.01 | 80 | 10,000 |
| 0.03 | 150 | 19,000 |
| 0.3 | 0 | |
| Benzethonium chloride solution | | |
| 0.00001 | 30 | 3,800 |
| 0.00003 | 55 | 7,000 |
| 0.0001 | 70 | 9,000 |
| 0.0003 | 110 | 14,000 |
| 0.001 | 130 | 16,500 |
| 0.01 | 20 | 2,500 |
| Lauryl pyridinium chloride solution | | |
| 0.0005 | 0 | |
| 0.001 | 17 | 2,000 |
| 0.003 | 40 | 5,000 |
| 0.01 | 70 | 8,500 |
| 0.03 | 80 | 9,800 |
| 0.3 | 50 | 6,100 |
| Trimethyl stearyl ammonium chloride solution | | |
| 0.0005 | 20 | 3,000 |
| 0.001 | 50 | 7,300 |
| 0.003 | 70 | 10,500 |
| 0.01 | 95 | 14,000 |
| 0.03 | 85 | 12,000 |
| 0.05 | 80 | 11,000 |

EXAMPLE 2

Example 2 was repeated, but carboxymethyl cellulose cotton fiber (Product No. 24) was employed as adsorbent.

The results are listed in Table 5.

TABLE 5

| Concentration (%) | Recovery of Activities (%) | Activities per mg of protein (I.U.) |
|---|---|---|
| Benzalkonium chloride solution | | |
| 0.001 | 0 | |
| 0.003 | 30 | 3,500 |
| 0.01 | 105 | 13,000 |
| 0.03 | 145 | 18,000 |
| 0.3 | 0 | |
| Benzethonium chloride solution | | |
| 0.00001 | 25 | 3,500 |
| 0.00003 | 60 | 7,200 |
| 0.0001 | 70 | 9,000 |
| 0.0003 | 100 | 13,500 |
| 0.001 | 120 | 15,000 |
| 0.01 | 20 | 2,000 |
| Lauryl pyridinium chloride solution | | |
| 0.0005 | 0 | |
| 0.001 | 15 | 2,000 |
| 0.003 | 35 | 4,500 |
| 0.01 | 75 | 9,000 |
| 0.03 | 85 | 10,000 |
| 0.3 | 45 | 6,000 |
| Trimethyl stearyl ammonium chloride solution | | |
| 0.0005 | 20 | 3,000 |
| 0.001 | 45 | 7,000 |
| 0.003 | 75 | 11,000 |
| 0.01 | 90 | 13,000 |
| 0.03 | 85 | 12,000 |
| 0.05 | 80 | 10,000 |

It was observed that in all examples, the amount of urokinase activity eluted increased by about 50% when the concentration of sodium chloride in the elution buffer was increased to 0.5 M (pH 8.0).

Conventional eluting methods were employed.

The cationic surfactants can be easily removed by conventional means such as dialysis, or by the use of molecular sieves, membrane filters, or dextran gels.

Protein values reported herein were determined by Lowry's method using Folin reagent. Samples were dialyzed before measurement. The standard material for this measurement is purified bovine serum albumin. For confirmation, such protein content was also determined by the biuret method.

Thromboplastin-like materials were determined by measuring the shortening of plasma recalcification time with conventional methods using Plasma-Coagulation-Control (lyophylized human citrated plasma produced by Ortho Co., Inc.). Samples were dialyzed against saline before measurement. Standard material for thromboplastin activity is Ortho Brain Thomboplastin (lyophylized rabbit brain thromboplastin produced by Ortho Co., Inc.). Detection of plasma clots is so difficult at high urokinase concentration with conventional means that coagulation time was measured by thromboelastograph (Hellige Co., Inc.).

Based upon the fibrinolytic activity in the plasma clot measured by thromboelastograph, urokinase obtained in the present invention has highly thrombolytic activity.

The following additional non-limiting examples further illustrate the invention.

EXAMPLE 3

Three grams of carboxymethyl cellulose powder for chromatography produced by Serva Co., Inc. were packed in each of six 9 ml-columns. 100 ml of urine of adult males having activity of 560 I.U. were diluted with water and passed through each column at 5° C. The amount of urokinase adsorbed to the carboxymethyl cellulose powder was 510 I.U. per column. Each column was washed with 0.1 M sodium chloride solution and eluted at 25° C. with 25 ml of one of the cationic surfactants shown in Table 6. The activity concentration and specific activities of urokinase in the initial human urine were 5.6 units/ml, and 40 units/1 mg of protein. Results are listed in Table 6.

As is evident from Table 6, urokinase is not eluted with aqueous ammonia at pH 8.0 (5° C.), but can be eluted with the cationic surfactant solutions at the same pH. The cationic surfactants enhance urokinase activities, and therefore, recovery of urokinase activities is more than 100 percent. It is evident that the cationic surfactants in the specified concentration used enhanced urokinase activities by 1.2 to 1.5 times. It appears that recovery of urokinase is more than 90 percent. Specific activities of urokinase obtained were 11,000 to 15,000 I.U. per 1 mg of protein. It follows that urokinase was purified about 300 times as much.

When urokinase was eluted with aqueous ammonia of pH 11.8 (5° C.) as the eluting agent, the recovered urokinase activities were only 55 and specific activity of the eluted urokinase solution was only 440 I.U. per 1 mg of protein.

TABLE 6

| Column No. | Composition of Eluting Solution | | | Activities of Eluted Urokinase | Recovery of Activities | Activities per mg of Protein | Rate of* Purification |
|---|---|---|---|---|---|---|---|
| | NaCl | pH value (Aqueous NH₃) | Cationic Surfactants (W/V %) | | | | |
| 1 | 0.5M | 8.0 | 0 | 0 I.U. | 0% | 0 I.U. | -times |
| 2 | " | " | 0.01% of Benzalkonium Chloride | 605 | 120 | 15,000 | 375 |
| 3 | " | " | 0.0002% of Benzethonium Chloride | 560 | 110 | 14,000 | 350 |
| 4 | " | " | 0.03% of Stearyl-Trimethyl Ammonium Chloride | 670 | 130 | 12,500 | 313 |
| 5 | " | " | 0.05% of Lauryl Pyridinium Chloride | 680 | 135 | 11,000 | 275 |
| 6 | " | 11.8 | 0 | 280 | 55 | 440 | 11 |

*Rate of Purification:
Specific activities of purified urokinase per specific activities of raw urokinase.

EXAMPLE 4

Fifty Ml of urine from adult men were passed at 5° C. through the column packed with 1 g of polyacrylonitrile synthetic fibers (Vonnel). The column was washed with water. Then 15 ml of 0.01 M Na₂HPO₄-NaH₂PO₄, 0.5 M NaCl buffer solution (pH=7.2 at 5° C.) containing 0.003% benzalkonium chloride (produced by Takedayakuhin Kogyo Co., Inc.) were passed through the column at 5° C. and 120 I.U. of urokinase activity were eluted.

Since the total urokinase activity of the starting material was 175 I.U. and activity of urokinase adsorbed to the adsorbent was 105 I.U., 114 percent of urokinase adsorbed was eluted.

When after the adsorbing of urokinase in the above experiment, 0.01 M $Na_2HPO_4$-$NaH_2PO_4$, 0.5 M NaCl buffer solution (pH=7.2 at 5° C.) having no benzalkonium chloride were passed through a column in the same manner as above, no urokinase could be eluted.

The experiment was repeated using Exlan as the polyacrylonitrile synthetic fibers instead of Vonnel. Substantially the same result was obtained.

EXAMPLE 5

0.15 Grams (0.5 ml) of diethylaminoethyl cellulose (produced by Brown Co., Inc.) were packed in a column. Through this column, 5 ml of crude urokinase 2200 I.U. per 1 mg of protein) derived from human urine having activities of 10,000 I.U. were passed. Activities of urokinase adsorbed in the column was 5,500 I.U. Through this column, 2 ml of 0.01 M $Na_2HPO_4$-$NaH_2PO_4$, 0.3 M NaCl buffer solution (pH=6.0 at 5° C.) having 0.02% (W/V) benzalkonium chloride as eluting agent were passed. Urokinase of 6,600 I.U. was obtained. Recovery of urokinase was 125 percent. Specific activities of urokinase obtained were 92,000 I.U. per 1 mg of protein.

When, after the adsorbing of urokinase in the above experiment, 2 ml of 0.01 M $Na_2HPO_4$-$Na_2HPO_4$, 0.3 M NaCl buffer solution (pH=7.2 at 5° C.) without benzalkonium chloride were passed through a column in the same manner as above, only 300 I.U. of urokinase activity were obtained. Recovery or urokinase was 5 percent.

As is evident from these results, urokinase can be eluted more profitably by employment of benzalkonium salt in accordance with the present invention.

EXAMPLE 6

50 Grams (500 ml) of carboxymethylated cotton having a degree of carboxymethyl substitution of 0.168 were packed in a 106 mm×57 mm column. 100 l of human urine obtained by diluting 50 l of adult male urine with 50 l of water were passed through such column at 20° C. under SV of 36. There was no decrease rate of passage through the column during adsorption.

The ratio of urokinase adsorbed to urokinase charged was more than 95 percent. Activities of adsorbed urokinase per 1 g of dried carboxymethylated cotton was 5,500 I.U. The efficiency of treating human urine was 36 RV per hour. The duration of this experiment was 5.5 hours.

Soon after such treatment, 1,250 ml of 0.01 M $Na_2HPO_4$-$NaH_2PO_4$, 0.5 M NaCl, 0.02% (W/V) benzalkonium chloride buffer solution (pH=0.0 at 5° C.) were passed through the column at 5° C. and the adsorbed materials were eluted. The eluate containing urokinase was neutralized with hydrochloric acid solution. This eluate had urokinase activity of 385,000 I.U.

Recovery of urokinase activities in the complete operation (adsorption and elution of urokinase) was 140 percent. Therefore, 7,700 I.U. of urokinase per 1 mg of dried carboxymethylated cotton was recovered.

The experiments were repeated with carboxymethyl cellulose samples with degrees of substitution of 0.06 and 0.22. With the former, less than 30 percent of urokinase was adsorbed. With the latter, human urine did not pass through and the urokinase activity in the urine was lost.

The following experiment was conducted for comparison with the present invention.

150 Grams (500 ml) of carboxymethyl cellulose powder for chromatography (produced by Serva Co., Inc.) were packed in a column (106 mm×57 mm). 100 l of human urine obtained by diluting 50 l of adult male urine with 50 l of water were passed through the column at 20° C.

From the start of the operation the current speed of the charged urine decreased, and continued to do so during the experiment. In the first hour, 1.5 l of urine passed, but in the first 6 hours only 3 l of urine passed. After 6 hours, no additional urine could pass through the column.

Urokinase was recovered as described above.

Since only 3 l of human urine with a total activity of urokinase: 15,000 I.U. can be processed, it is clear that the procedure could not be employed industrially. The results of the experiment were analyzed. 90 Percent of the urokinase was adsorbed in the column.

The carboxymethyl cellulose with adsorbed urokinase was divided into two equal part.

One part was mixed at 5° C. with 750 ml of aqueous ammonia of pH 11.8, and the other part was mixed with 750 ml of 0.01 M $Na_2HPO_4$-$NaH_2PO_4$, 0.5 M NaCl, 0.02% (W/V) benzalkonium chloride buffer solution (pH=0.0 at 5° C.). The eluate containing urokinase was separated from carboxymethyl cellulose powder by centrifugation.

In the first instance, the activity of urokinase recovered by elution was 5,400 I.U. (recovery: 36%). In the second case, the activity of urokinase recovered was 10,800 I.U. (recovery: 71%).

The advantages of the process of this invention are evident from the foregoing.

The above experiment was repeated using other carboxymethyl cellulose powders for chromatography (produced by both Brown Co., Inc. and Whatman Co., Inc., respectively) with substantially the same results.

EXAMPLE 7

0.7 Grams carboxymethyl cellulose powder for chromatography (CM-32 of Whatman Co., Inc.) were packed in a column (2 ml, l/d=5). Through this column, 100 ml of crude urokinase solution (100 I.U./ml, specific activity=2,000 I.U./mg of protein, containing thromboplastin activity corresponding to 1 mg. of rabbit brain thromboplastin; the thromboplastin/urokinase ratio was 0.1 µg/I.U.) with activity of 10,000 I.U. derived from human urine were passed at 5° C. The thus obtained carboxymethyl cellulose column was washed with water. 1 M NaCl, 0.01% (W/V) benzalkonium chloride aqueous solution was adjusted to pH 9.0 at 5° C. with addition of a small amount of aqueous ammonia to produce the eluting agent. 25 ml of eluting agent were passed through the column at 5° C. at a flow rate of 5 ml/hr, and the eluate was collected by fraction collector.

Urokinase activities of 11,000 I.U. were recovered in fractions 0–2 RV (between 0 and 4 ml) from the beginning. 110 Percent of urokinase adsorbed was recovered in this fraction. Specific activity of urokinase in this fraction was 41,000 I.U./mg of protein (purification of 20.5 times as much; thromboplastin activity = 100 µg, ratio of thromboplastin/urokinase = 0.01 µg/1 I.u). This ratio decreased by this operation. Accordingly, highly purified urokinase wth only trace thromboplastin was recovered in high yield.

From the fraction 8-10 RV (between 16 and 20 ml) of eluate, 450 µg of thromboplastin activity (recovery = 45%) were recovered. Urokinase activity was not found. Accordingly, 55 percent of thombopastin in thromboplastin solution charged was recovered in the whole eluate.

As is evident from the Examples, the process of the invention makes possible the recovery of highly purified urokinase as well as materials with thromboplastin activity. It is thus possible to separate these activities.

The elution pattern is shown in FIG. 1.

Thromboplastin activities were calculated in the same manner as above.

What is claimed is:

1. A process for the production of urokinase from human urine in which urine or a dilute aqueous mixture thereof is adsorbed on an adsorbent for urokinase and thereafter eluted with an aqueous cationic surfactant mixture at a pH of from 6 to 9 and a surfactant concentration which is effective for eluting urokinase.

2. A process as in claim 1 wherein the adsorbent is selected from the group consisting of cation exchange resins, carboxyalkyl cellulose wherein the alkyl groups contain up to four carbon atoms, carboxymethyl Sephadex, polyacrylonitrile resin fiber, silica gel-bentonite, diethylaminoethyl Sephadex and phosphocellulose.

3. A process as in claim 1 in which the adsorbent is carboxyalkyl cellulose in fiber form in which the alkyl groups contain up to four carbon atoms.

4. A process as in claim 1 wherein the ratio of water to urine is 0.5 to 12 g water per gram of urine.

5. A process as in claim 2 wherein the carboxyalkyl cellulose is in fiber form.

6. A process as in claim 1 conducted in a column and elution is continued after desorption of urokinase activity to desorb thromboplastin activity.

7. A process as in claim 1 wherein the surfactant is a benzalkonium salt, and the concentration is $3 \times 10^{-3}$ to $3 \times 10^{-2}$%.

8. A process as in claim 1 wherein the surfactant is a benzethonium salt and the concentration is from $1 \times 10^{-5}$ to $1 \times 10^{-2}$%.

9. A process as in claim 1 wherein the surfactant is a lauryl pyridinium salt and the concentration is from $1 \times 10^{-3}$ to $3 \times 10^{-1}$%.

10. A process as in claim 1 wherein the surfactant is a stearyl-trimethyl ammonium salt and the concentration is from $5 \times 10^{-4}$ to $5 \times 10^{-2}$%.

11. A process as in claim 1 wherein said urine or a dilute aqueous mixture thereof is crude urokinase solution.

12. A process as in claim 1 wherein the elution operation of urokinase is stopped before elution of thromboplastin activity.

* * * * *